「(12) United States Patent
Lu et al.

(10) Patent No.: US 6,896,700 B2
(45) Date of Patent: May 24, 2005

(54) TRI-LEAFLET MECHANICAL HEART VALVE

(75) Inventors: Po-Chien Lu, Taipei (TW); Ren-Hong Huang, Gongguan (TW); Shu-Hsun Chu, Taipei (TW)

(73) Assignee: Tamkang University, Taipei (TW)

( * ) Notice: Subject to any disclaimer, the term of this patent is extended or adjusted under 35 U.S.C. 154(b) by 0 days.

(21) Appl. No.: 10/629,702

(22) Filed: Jul. 30, 2003

(65) Prior Publication Data

US 2004/0249451 A1 Dec. 9, 2004

(30) Foreign Application Priority Data

Jun. 6, 2003 (TW) ..................................... 92210371 U

(51) Int. Cl.[7] ................................................. A61F 2/24
(52) U.S. Cl. ...................... 623/2.34; 623/2.2; 623/2.22
(58) Field of Search ................................. 623/2.2–2.34

(56) References Cited

U.S. PATENT DOCUMENTS 5,123,918 A * 6/1992 Perrier et al. ............... 623/2.23
5,405,381 A * 4/1995 Olin ........................... 623/2.22
5,628,791 A * 5/1997 Bokros et al. .............. 623/2.19

* cited by examiner

Primary Examiner—David J. Isabella
(74) Attorney, Agent, or Firm—Rosenberg, Klein & Lee

(57) ABSTRACT

A tri-leaflet heart valve includes an annular valve base with an inner surface forming an orifice through which blood flows from the upstream side to the downstream side. Three protruding hinges, each with concave sockets on opposite sides, are formed on the inner surface. Each hinge has a downstream face and an upstream face connected by a ridge. Three leaflets are respectively arranged between adjacent hinges. Each leaflet has round pivots on both sides that rest inside the concave sockets, allowing the leaflets to freely rotate in the annular valve base. When the leaflets are subject to a positive pressure from the blood flow, the leaflets are pushed open and allow a central flow. When the leaflets are subject to a negative pressure, the leaflets are closed to occlude the blood flow.

6 Claims, 5 Drawing Sheets

TRI-LEAFLET MECHANICAL HEART VALVE

BACKGROUND OF THE INVENTION

1. Field of the Invention

The present invention relates generally to the field of artificial mechanical heart valves (MHV), and in particular to a tri-leaflet MHV with a smooth and streamlined curved surface that effectively prevents clotting and hemolysis while forming a sturdy and firm seal when closed.

2. Description of Prior Technology

Heart valve replacement surgery is one of the most mature and effective therapies for valvular diseases. This type of operation has become a regular surgical procedure since the commercialization of the first artificial heart valve in 1966. Clinically, the postoperative death rate is below 5%. On average, successful heart valve implantation may extend patient life for more than 10 years. Currently, the demand for artificial heart valve replacement surgery is approximately 200,000 patients each year.

Generally, there are two major types of artificial heart valves. The first type is the Mechanical Heart Valve (MHV), which is completely composed of artificial materials. The second type is the Bioprosthetic Heart Valve (BHV), which consists of chemically treated biomaterials. Pyrolytic carbon (PyC) has become the most commonly used material for MHV since it was first introduced for clinical implantation in 1969. Single leaflet and bi-leaflet MHVs made of PyC became common in the late 1970's and have since been used in the treatment of valvular diseases. Up to now, more than two million PyC heart valves have been implanted in human bodies and the accumulated clinical experience exceeds two hundred thousand patient-years.

BHVs are chemically treated animal valves, such as pig and ox. Their geometry is similar to the human valve and is thus commonly used by medical doctors. However, the BHV suffers from calcification and tissue regression, making it unsuitable for patients aged below 30.

Although MHV does not exhibit calcification and tissue regression, clinical reports indicate MHV often causes thrombosis and thromboembolism. The MHV patients must continuously take anticoagulants for life in order to reduce the risks of these complications. This has been one of the biggest problems with MHV implantation. The intake of anticoagulants may increase the incidence of hemorrhagic diseases and threaten the life of MHV patients. Moreover, long term medication may cause cardiac complications like endocarditis, hemolysis and so on. Although the incidence of cardiac complications is low, it cannot be neglected.

MHV basically contains one or more leaflets, an annular valve base, a hinge and a sewing ring. The leaflets are occluders for the opening and closing of the valve, which operates 0–200 times every minute inside the human body. The valve base serves as a frame for holding the occluders. The hinge rotatably supports the leaflets in the valve base. The sewing ring is a woven material surrounding the MHV for attachment to the implantation site. The leaflets, the annular valve base and the hinge still need improvements from the viewpoint of fluid dynamics.

Bi-leaflet heart valves form three streams when the two leaflets are opened, which is non-symmetric with respect to a center of the heart valve. Non-hermetic compliance with the aortic sinuses leads to non-symmetric flow profile, thus inducing a large velocity gradient and turbulence. Since the bi-leaflet MHV is centrally asymmetric, the two leaflets are not opened synchronously, leading to great recirculation of blood and increasing the burden of heart. To overcome such deficiencies, new tri-leaflet heart valves are continuously designed.

Hemodynamically, the tri-leaflet heart valve opens to form a single central flow, similar to the operation of the human aortic valve. The pressure induced by the circulation of blood inside semi-circular aortic sinuses downstream the heart valve helps to open and close the heart valve. The most important factors in the design of the tri-leaflet heart valve are the shape of the leaflets and the pivoting mechanism.

Conventional tri-leaflet heart valve designs use protruding supports to control the opening of leaflets. For example, U.S. Pat. No. 5,843,183 discloses a support member that extends from the annular valve base to support the corresponding leaflet. Leaflet movement from open to closed position is controlled both by upstream retainers aligned with the flat central sections of each leaflet and by surfaces on the side walls of the projections along which the leaflets slide. In U.S. Pat. No. 6,395,024, two support members support each corresponding leaflet. The disadvantage associated with these prior designs is that the support member and the leaflet will create wakes and turbulence of the blood flow.

Other examples of conventional tri-leaflet heart valves are disclosed in U.S. Pat. Nos. 4,446,577 and 5,522,886, wherein a pair of projections on the sides of the leaflet fit into slots inside the annular valve base and pivotally support the leaflet. In U.S. Pat. No. 5,628,791, a boss slides and rotates inside the slot to control the leaflet The complicated manufacturing process and occurrence of thrombosis are the main disadvantages.

SUMMARY OF THE INVENTION

The conventional tri-leaflet heart valves that employ support members extending out of the annular valve base suffer from the disadvantage of wake and turbulence created in the blood flow through the heart valve. The drawbacks of other tri-leaflet heart valves include a complicated manufacturing process to form deep slots in the annular valve base and bosses on the leaflets that rotatably fit into the slots, which lead to thromboembolism.

To overcome the deficiencies of conventional tri-leaflet heart valves, the present inventor designed a new tri-leaflet heart valve that was issued Taiwan Utility Model No. 134683. Although working well, the design can be further improved in the leaflet structure, the annular valve base and the pivoting joint.

Thus, the primary objective of the present invention provides a tri-leaflet heart valve that has a central flow hemodynamic configuration similar to the human aortic valve. The pressure induced by blood circulation inside the semi-circular aortic sinuses downstream the heart valve assists in opening and closing the leaflets.

Another goal of the present invention is to provide a tri-leaflet heart valve that effectively eliminates the occurrence of thrombosis. A pivot joint between the leaflet and the annular valve base is formed by a curved projection and semi-circular smooth socket in the valve base, which allows for rotation and sliding of the leaflet with respect to the valve base. The leaflet is loosely supported by the projection, which minimizes the mechanical resistance against leaflet movement and allows for washing effect to minimize thrombosis.

This tri-leaflet heart valve also aims to provide excellent sealing effect, wherein the annular valve base forms a small socket and a ridge to maintain the leaflets sealed when the valve is closed.

A further objective of the present design is to allow a perpendicular opening angle. The protruding hinges of the valve base has a downstream inclination that supports and fixes the leaflet at a desired orientation when the heart valve is opened.

To overcome the deficiencies of previous designs, the present invention provides a tri-leaflet heart valve with an annular valve base with three protruding hinges on the inner surface. Each protrusion has a concave socket on both the upstream face and downstream face connected by a ridge. Three fan-shaped leaflets with curved configuration are fit into the annular valve base. Each leaflet has rounded ends on both of the bottom edges that serve as hinges inside the corresponding concave sockets in which the leaflets are allowed to rotate freely. When the leaflets are subject to a positive pressure of the blood flow, the leaflets are opened to allow blood flow through a central orifice. Under negative pressure, the leaflets are closed to occlude the central opening.

Notches are built into the bottom of the leaflets, from which the smooth outward projection forms the hinge. The leaflets have no sharp projections and allow for smooth blood flow. The side edges adjacent leaflets contact each other when the heart valve is closed. The leaflet has a curved inner surface that forms a recessed surface of the annular valve base. When the leaflets are opened, the downstream inclination on the annular valve base provides support to maintain the leaflet at the desired angle.

BRIEF DESCRIPTION OF THE DRAWINGS

The present invention will be apparent to experts via the following descriptions with reference to the attached drawings, in which.

DETAILED DESCRIPTION OF PREFERRED DESIGN

Figure 1:
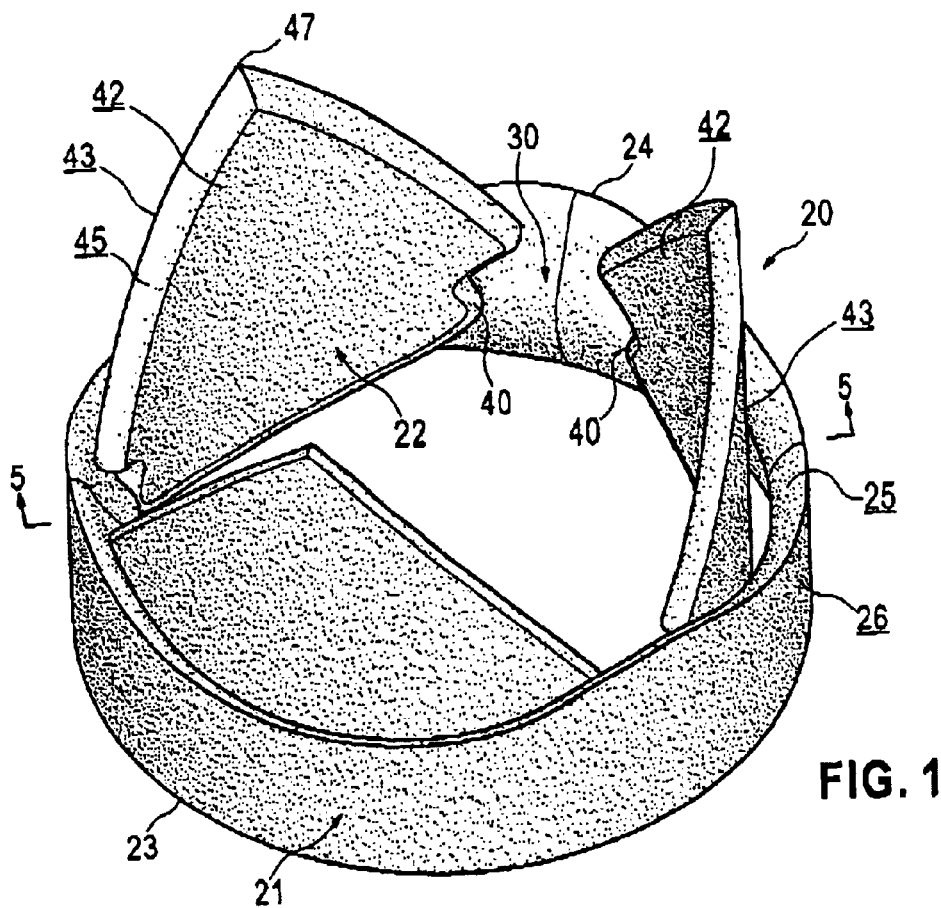
FIG. 1 is a perspective view of a tri-leaflet heart valve constructed in accordance with the present invention in an open conformation.
Figure 2:
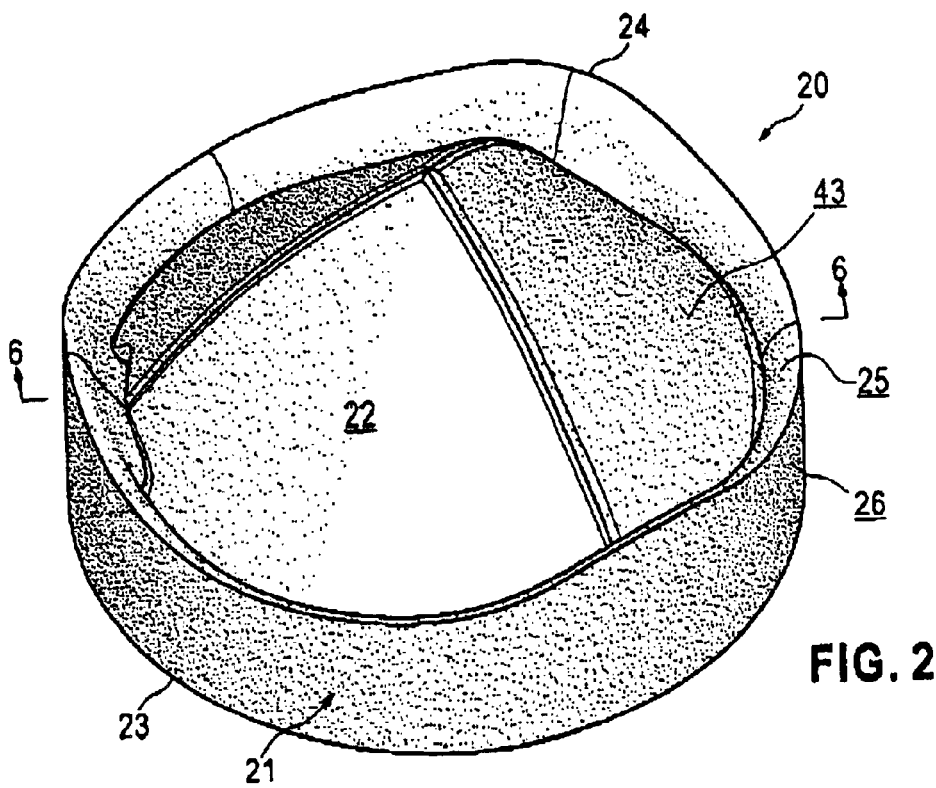
FIG. 2 is a perspective view of the tri-leaflet heart valve in a closed conformation.

In reference to the drawings and in particular to FIGS. 1 and 2, a tri-leaflet heart valve constructed in accordance with the present invention, generally designated with reference numeral 20, contains an annular valve base 21, three leaflets 22 and three hinges 30 formed on the inner surface (not labeled) of the annular valve base 21 in an equally spaced manner for rotatably mounting the leaflets 22. The leaflets 22 are allowed to rotate freely with respect to the annular valve base 21 for opening and closing the heart valve 20. The heart valve 20 functions as a one-way valve by means of which blood is allowed to flow from the upstream side to the downstream side of the valve 20, but not in the opposite direction. Stagnation and turbulence in blood flow are generally avoided when the blood is flowing through the valve in order to reduce thrombosis and hemolysis.

Figure 3:
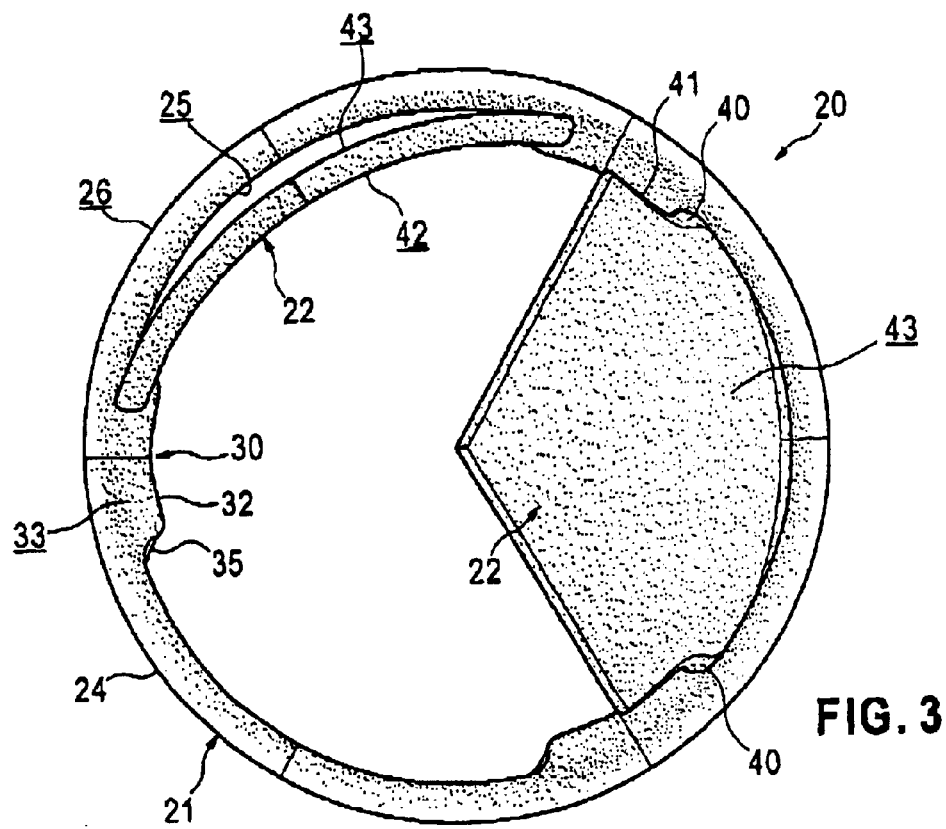
FIG. 3 is a top view of the tri-leaflet heart valve with one leaflet removed, one leaflet opened and the third leaflet closed.
Figure 4:
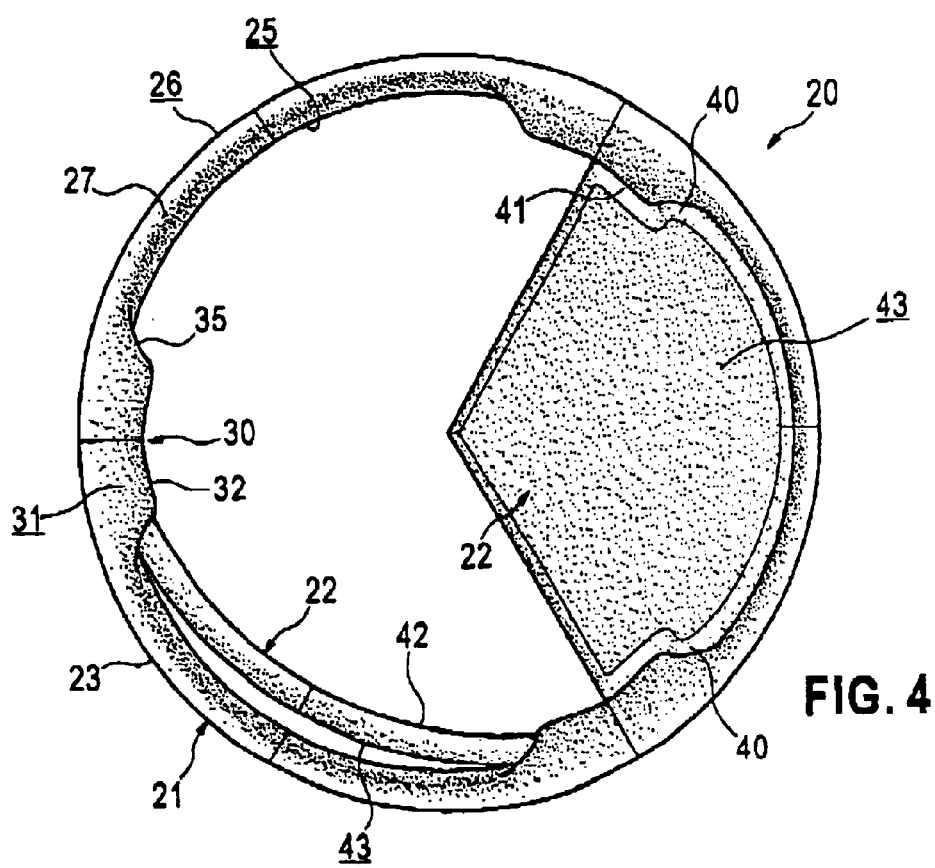
FIG. 4 is a bottom view of the tri-leaflet heart valve shown in FIG. 3.

Referring to FIGS. 3 and 4, which are respectively top and bottom views of the heart valve 20 with one leaflet removed, one opened and the third one closed, each of the hinges 30 consists of a curved upstream face 31 and a curved downstream face 33 connected by a rounded ridge 32. The hinge 30 also has concave sockets 35 on opposite ends in which the round pivots 40 of each leaflet 22 are inserted, serving as a hinge joint between the leaflet 22 and the annular valve base 21 and allowing the leaflet 22 to freely rotate with respect to the annular valve base 21.

Each leaflet 22 is positioned between adjacent hinges 30. The leaflet 22 has round pivots 40 on both sides rotatably received in and supported by the concave sockets 35 of the adjacent protruding hinges 30. Rotation of the leaflet 22 with respect to the annular valve base 21 about the pivots 40 thereby opens and closes the heart valve 20.

The leaflets 22 are fan-shaped plates with a smooth curved surface. When the leaflets 22 are fully opened, a maximum opening area is available in the heart valve 20, forming a single, central blood flow for the best hemodynamic results. In comparison, the conventional bi-leaflet heart valve forms three streams of blood flow, which is susceptible to separation at the boundary layer and turbulence, causing damage to the blood cells and formation of thrombosis. Conventional tri-leaflet heart valves have flat leaflets, that form a triangular opening at the center of the valve and crescent-shaped, secondary openings between the leaflets and the inner surface of the valve base, leading to four streams of blood.

The leaflet 22 of the present invention forms a triangle with two side edges 45 extending from an apex 47 that points downstream and a curved bottom edge 46 which forms a mating face (not labeled). The side edges 45 are configured so that, when the heart valve 20 is closed, the side edges 45 of adjacent leaflets 22 tightly engage each other, while the mating face of the bottom edge 46 contacts a curved recess 27 to occlude the heart valve 20. The recess 27 is formed on the inner upstream surface of the annular valve base 21 and complementary in geometry to the mating face of the bottom edge 46 of the leaflet 22 whereby a tight seal is formed between the leaflets 22 and the annular valve base 21 when the heart valve 20 is closed.

Figure 5:
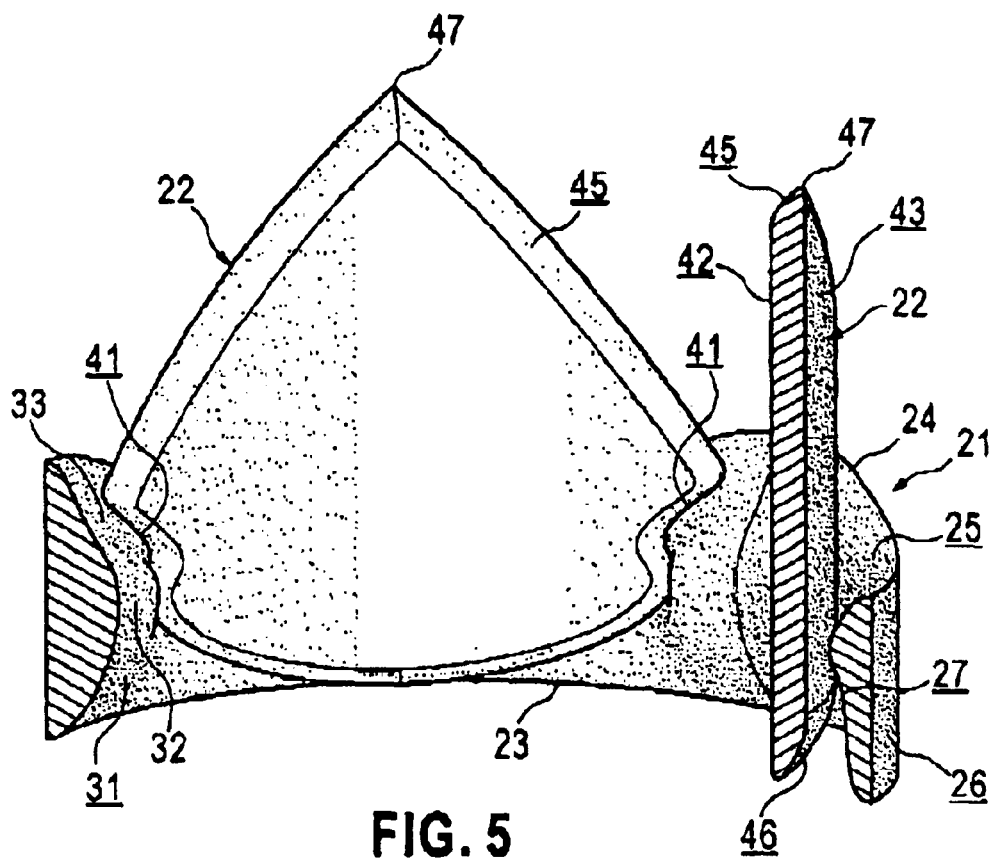
FIG. 5 is a cross-sectional view taken along line 5—5 of FIG. 1.
Figure 6:
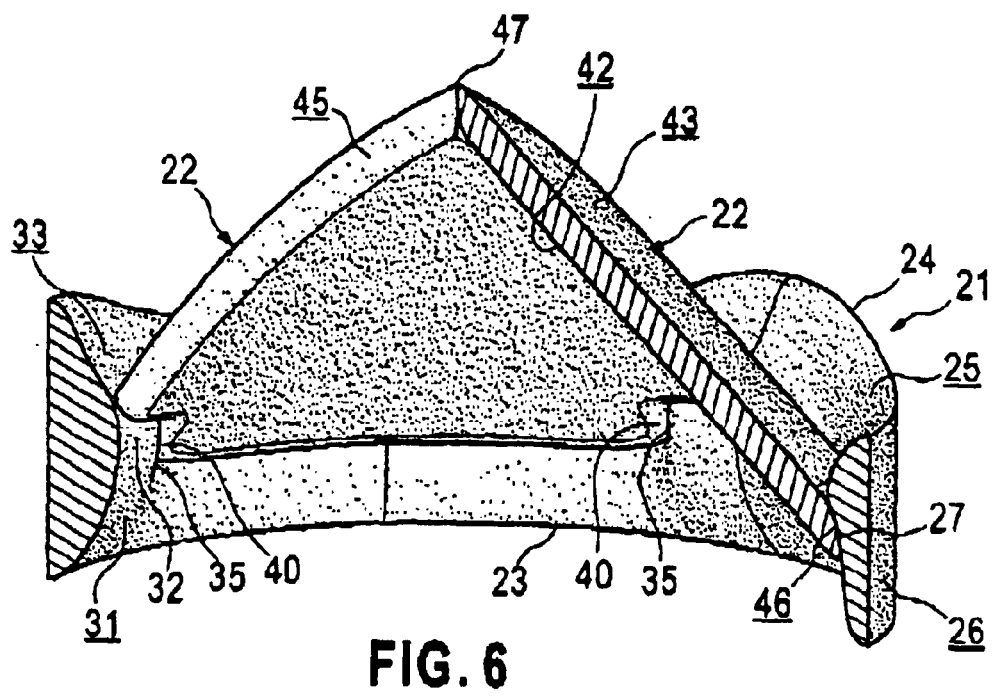
FIG. 6 is a cross-sectional view taken along line 6—6 of FIG. 2.

FIG. 5 is a cross-sectional view taken along line 5—5 of FIG. 1 showing the fully open heart valve 20, while FIG. 6 is a cross-sectional view taken along line 6—6 of FIG. 2 showing the closed heart valve 20. The opening/closing operation of the heart valve 20 is thus illustrated in both drawings.

When the heart valve 20 is fully opened, the leaflets 22 rotate about the round pivots 40 retained in the concave sockets 35 of the protruding hinge 30 until a stop edge 41, formed between each side edge 45 and the bottom edge 46 in the form of a curved notch 48, physically engages the downstream face 33 of the hinge 30 to maintain the leaflet 22 in a position substantially parallel to the blood flow, thus allowing the maximum flow of blood. When the heart valve 20 is closed, the side edges 45 of the leaflets 22 engage each other and the apexes 47 coincide with each other. The curved faces of the bottom edges 46 of the leaflets 22 tightly engage the corresponding upstream recesses 27 of the annular valve base 21. Thus, the leaflets 22, the hinges 30 and the upstream recessed face 27 of the annular valve base 21 together form a continuous and smooth surface with no undesired sharp projections. This configuration allows for induction of smooth flow field.

Figure 7:
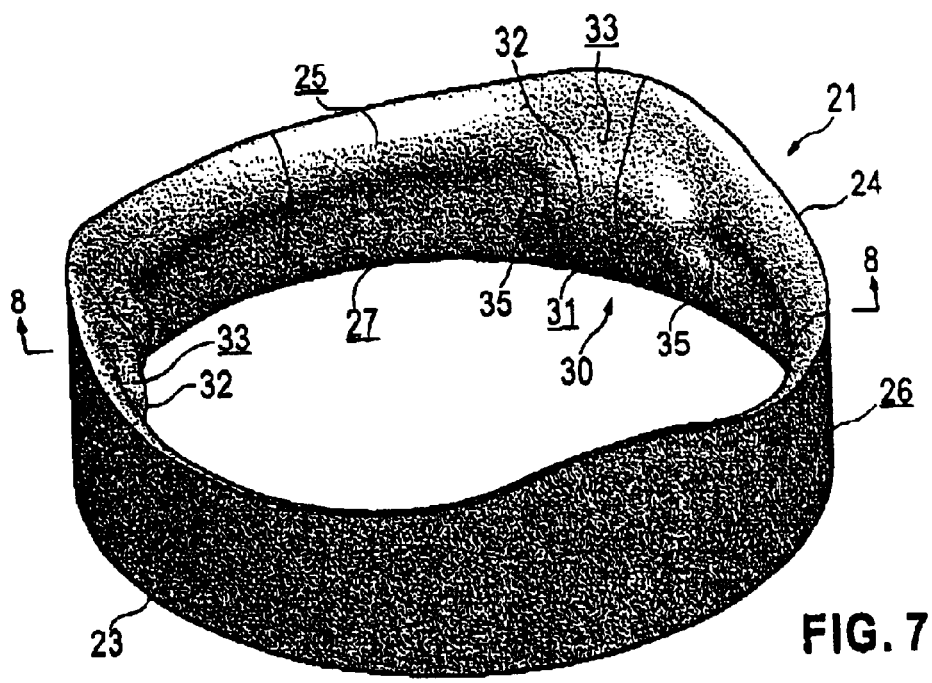
FIG. 7 is a perspective view of the annular valve base of the tri-leaflet heart valve.
Figure 8:
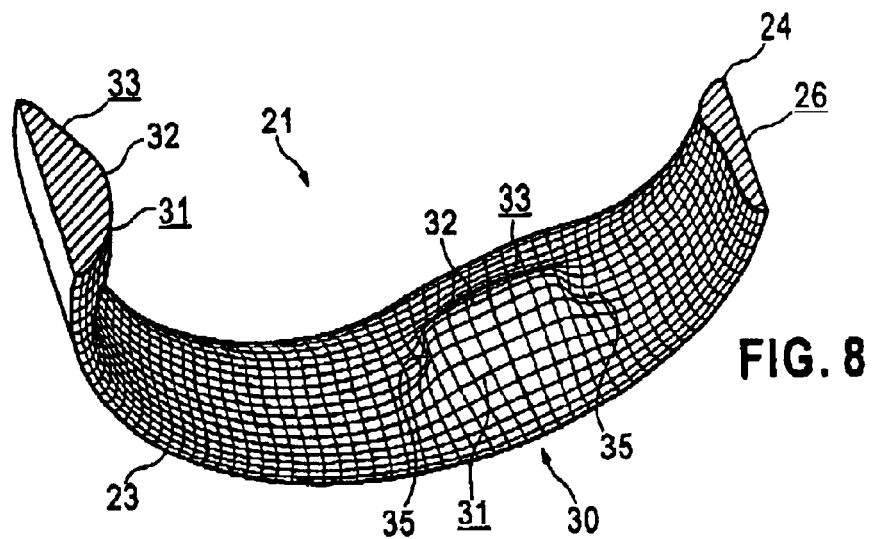
FIG. 8 is a perspective view, partly cut away along line 8—8 of FIG. 7, of the annular valve base illustrated with grid surface.
Figure 9:
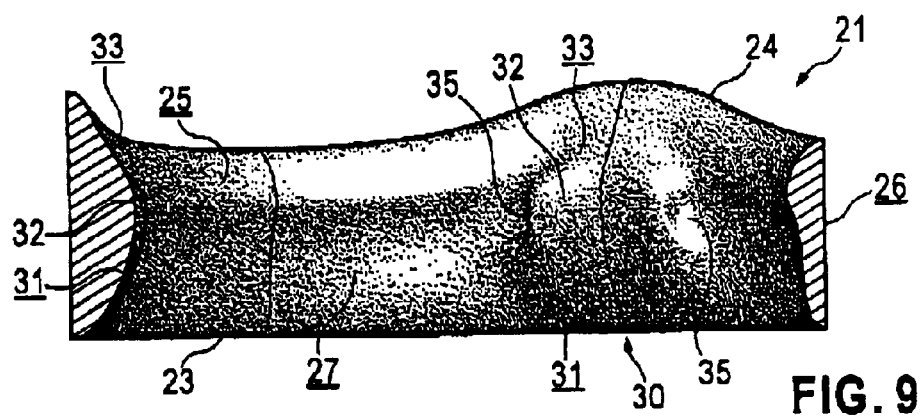
FIG. 9 is a cross-sectional view taken along line 8—8 of FIG. 7.

In FIGS. 7–9, which are a perspective view and cross-sectional views of the annular valve base 21, the curved upstream recesses 27 are found on the inner surface of the annular valve base 21. The annular base also has an upstream circumferential edge 23, an opposite downstream circumferential edge 24, and outer surface 26. A circumferential step like configuration is formed along the inner surface by the raised downstream surface 25 and the upstream recesses 27 with which the curved bottom edges 46 of the leaflets 22 contact and form a tight seal.

When the heart valve 20 is opened, the stop edge 41 of each leaflet 22 contacts the corresponding downstream face 33 of the protruding hinge 30. When the heart valve 20 is closed, the curved bottom edges 46 of the leaflets 22 contact the upstream recesses 27 of the annular valve base 21 with the stop edge 41 engaging the curved ridge 32 of the hinge 30. This maintains the rotation of the leaflet 22 while effectively retaining the leaflet 22 inside the annular valve base 21. The ridge 32 also tightly seals with the notch 48 of the leaflet 22 when the valve 20 is closed.

The downstream face 33 of the hinge 30 of the annular valve base 21 limits the rotation of the leaflet 22 with respect to the annular valve base 21 when the heart valve 20 is opened. The leaflet 22 is maintained at 90 degrees with respect to the annular valve base 21, thus allowing maximum flow area. In comparison, the pivoting structure of the conventional artificial heart valve is formed by a grooved recess, which may lead to stagnation, separation of the blood flow, and thromboembolism The present invention eliminates this problem.

Figure 10:
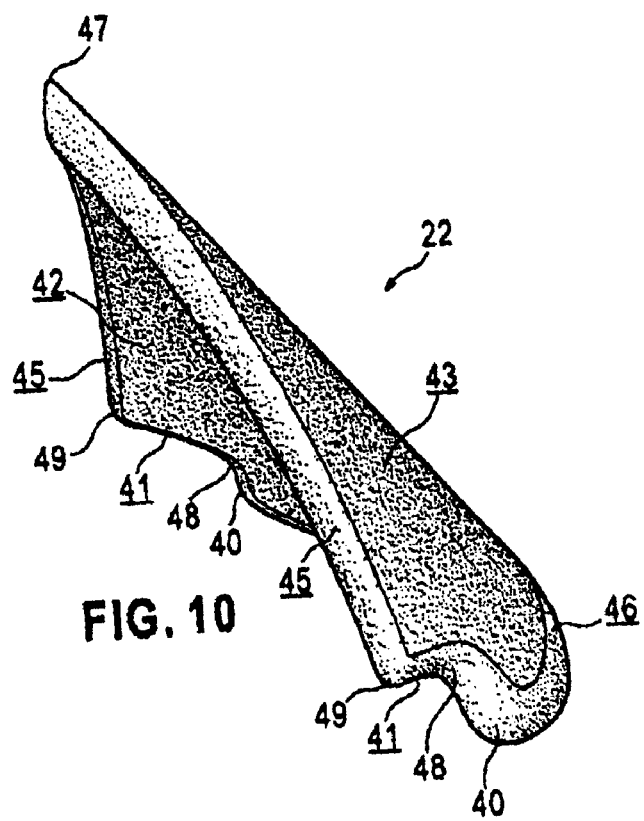
FIG. 10 is a perspective view of a leaflet of the tri-leaflet heart valve.
Figure 11:
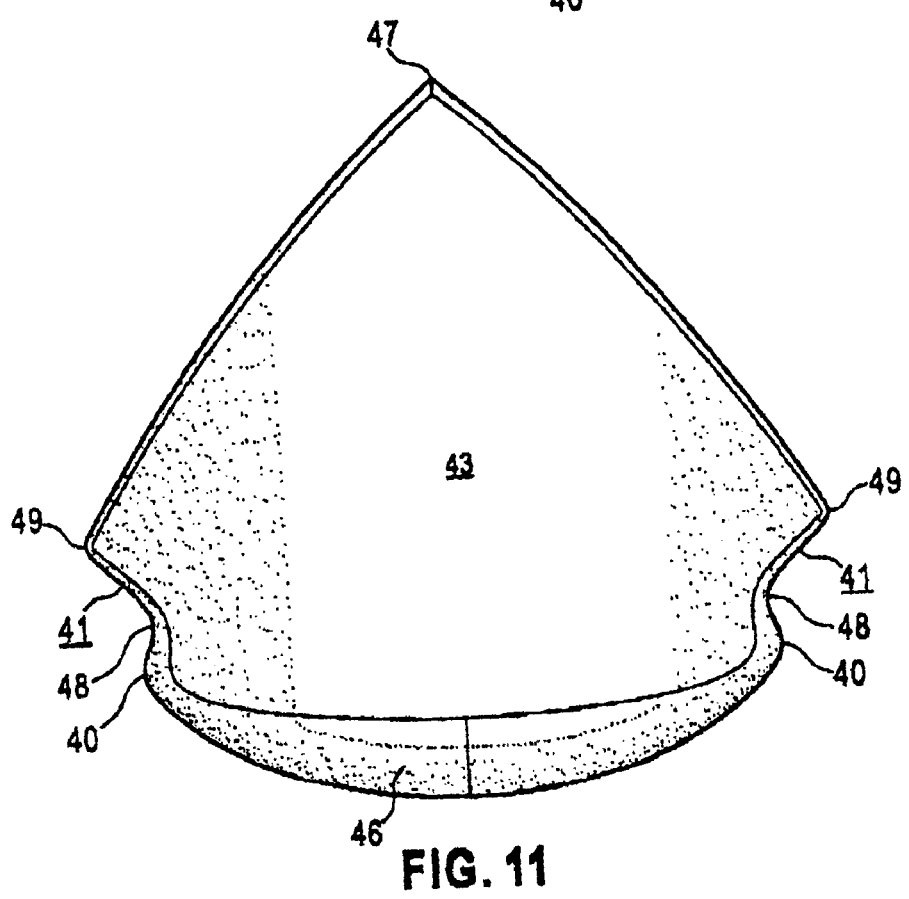
FIG. 11 is a top view of the leaflet of the tri-leaflet heart valve.

FIG. 10 is a perspective view of the leaflet 22 of the present invention, while FIG. 11 is the top view. The leaflet 22 is a curved fan-shaped plate with a concave inner surface 42 and convex outer surface 43, as well as the round pivots 40, the side edges 45 extending from the downstream apex 47 with the notches 48 right below the rounded tips 49, and the bottom edge 46. When the leaflets 22 close, the apexes 47 of the leaflets 22 contact each other, while the side edges 45 engage each other and the bottom edges 46 touch the upstream recesses 27 of the annular valve base 21. Thus, when the heart valve 20 is closed, a tight seal is formed between the leaflets 22 and the annular valve base 21 that minimizes leakage of blood.

When the leaflets 22 are subject to a positive pressure from the blood flow, they open to allow blood flow through the central orifice of the heart valve 20 from the upstream side to the downstream side. When the heart begins to contract, the blood is forced to flow through the heart valve 20, providing the positive pressure to rotate the leaflets 22 to their fully opened position. When the heart begins to expand, the pressure caused by circulation in the aortic sinus pushes the leaflets 22 toward the closed position. When the heart fully expands and creates negative pressure, the leaflets 22 are completely closed and occlude the blood flow through the heart valve 20. At this moment, as mentioned above, the annular valve base 21 and the leaflets 22 together form a continuous and smooth surface to effectively occlude the blood flow.

Although the present invention has been described with reference to the preferred design and operating mechanism, experts in the same field may make modifications and changes without departing from the scope of the present invention, which is defined by the following claims.

What is claimed is:

1. A tri-leaflet heart valve comprising:
   an annular valve base with an inner surface defining a central orifice through which a blood flow moves from an upstream side to a downstream side;
   three protruding hinges formed on the inner surface of the annular valve base and equally spaced along the inner surface of the annular valve base, each hinge comprising a convex downstream face connected to a convex upstream face by a curved ridge and a pair of concave sockets on opposite sides of the hinge; and
   three leaflets arranged between adjacent hinges, each leaflet having an arcuate contour and being provided with a pair of round pivots respectively mounted inside the concave sockets of the hinges, each of leaflets being respectively suspended between a corresponding pair of concave sockets and being freely rotatable within the annular valve base;
   when the leaflets are subject to a positive pressure from the blood flow, the leaflets are fully opened to allow the blood to flow through the central orifice, and when the leaflets are subject to a negative pressure, the leaflets are closed to occlude the blood flow.

2. The tri-leaflet heart valve as claimed in claim 1, wherein each leaflet is a fan-shaped plate with a smooth solid outer surface and a smooth inner surface, each being devoid of sharp projections; a downstream apex; a bottom edge and side edges where a curved notch, a stop edge and the round pivot are formed between each side edge and the bottom edge.

3. The tri-leaflet heart valve as claimed in claim 2, wherein the fan-shaped leaflet has the downstream apex from which the two side edges extend, and where the side edges of adjacent leaflets tightly seal with each other when the leaflets close.

4. The tri-leaflet heart valve as claimed in claim 2, wherein the fan-shaped leaflet has the bottom edge forming a tight seal with a corresponding upstream recess on the inner surface of the annular valve base when the leaflets are closed.

5. The tri-leaflet heart valve as claimed in claim 2, wherein a downstream surface of the inner surface of the annular valve base is configured to stop the rotation of the leaflet when the leaflet is opened, maintain it at a predetermined angle and form a seal between the smooth outer surface of the leaflet and the downstream surface of the inner surface of the annular valve base.

6. The ti-leaflet heart valve as claimed in claim 2, wherein the ridge of the protruding hinge is configured so that, when the leaflet is closed, the ridge forms a tight seal with the notches of the leaflet.

* * * * *